United States Patent
Gatenholm

(10) Patent No.: US 10,675,379 B2
(45) Date of Patent: Jun. 9, 2020

(54) CELLULOSE NANOFIBRILLAR BIOINK FOR 3D BIOPRINTING FOR CELL CULTURING, TISSUE ENGINEERING AND REGENERATIVE MEDICINE APPLICATIONS

(71) Applicant: CELLINK AB, Gothenburg (SE)

(72) Inventor: Paul Gatenholm, Riner, VA (US)

(73) Assignee: CELLINK AB, Gothenburg (SE)

(*) Notice: Subject to any disclaimer, the term of this patent is extended or adjusted under 35 U.S.C. 154(b) by 0 days.

(21) Appl. No.: 15/537,154

(22) PCT Filed: Dec. 18, 2015

(86) PCT No.: PCT/US2015/066755
§ 371 (c)(1),
(2) Date: Jun. 16, 2017

(87) PCT Pub. No.: WO2016/100856
PCT Pub. Date: Jun. 23, 2016

(65) Prior Publication Data
US 2017/0368225 A1    Dec. 28, 2017

Related U.S. Application Data

(60) Provisional application No. 62/093,881, filed on Dec. 18, 2014.

(51) Int. Cl.
*A61L 27/20* (2006.01)
*B33Y 80/00* (2015.01)
(Continued)

(52) U.S. Cl.
CPC .......... *A61L 27/20* (2013.01); *A61L 27/3817* (2013.01); *A61L 27/3882* (2013.01); *B33Y 40/00* (2014.12);
(Continued)

(58) Field of Classification Search
CPC ................... C08B 1/00; A23G 3/00
(Continued)

(56) References Cited

U.S. PATENT DOCUMENTS

| 6,103,790 A | 8/2000 | Cavaille et al. |
| 8,691,974 B2 | 4/2014 | Gatenholm et al. |

(Continued)

FOREIGN PATENT DOCUMENTS

| CN | 103893825 B | 6/2015 |
| EP | 2633032 B1 | 2/2015 |

(Continued)

OTHER PUBLICATIONS

Bäckdahl, H., Esguerra, M., Delbro, D., Risberg, B., and Gatenholm, P., Engineering microporosity in bacterial cellulose scaffolds, Journal of Tissue Engineering and Regenerative Medicine, 2 (6), 320-330 (2008).

(Continued)

*Primary Examiner* — Yashita Sharma
(74) *Attorney, Agent, or Firm* — New River Valley IP Law, P.C.; Michele L. Mayberry

(57) ABSTRACT

The present invention relates to biomaterial in the form of dispersion of cellulose nanofibrils with extraordinary shear thinning properties which can be converted into desire 3D shape using 3D Bioprinting technology. In this invention cellulose nanofibril dispersion, is processed through different mechanical, enzymatic and chemical steps to yield dispersion with desired morphological and rheological properties to be used as bioink in 3D Bioprinter. The processes are followed by purification, adjusting of osmolarity of the material and sterilization to yield biomaterial which has cytocompatibility and can be combined with living cells. Cellulose nanofibrils can be produced by microbial process but can also be isolated from plant secondary or primary cell (Continued)

wall, animals such as tunicates, algae and fungi. The present invention describes applications of this novel cellulose nanofibrillar bioink for 3D Bioprinting of tissue and organs with desired architecture.

32 Claims, 6 Drawing Sheets

(51) Int. Cl.

| | | |
|---|---|---|
| B33Y 70/00 | (2015.01) | |
| C08L 1/02 | (2006.01) | |
| C08B 15/08 | (2006.01) | |
| B33Y 40/00 | (2020.01) | |
| C09D 101/02 | (2006.01) | |
| A61L 27/38 | (2006.01) | |
| C09D 11/04 | (2006.01) | |
| C09D 11/14 | (2006.01) | |
| B82Y 5/00 | (2011.01) | |
| B82Y 15/00 | (2011.01) | |
| B29C 64/112 | (2017.01) | |
| A61F 2/04 | (2013.01) | |
| B29K 1/00 | (2006.01) | |
| B29L 31/00 | (2006.01) | |

(52) U.S. Cl.
CPC .............. *B33Y 70/00* (2014.12); *B33Y 80/00* (2014.12); *C08B 15/08* (2013.01); *C08L 1/02* (2013.01); *C09D 11/04* (2013.01); *C09D 11/14* (2013.01); *C09D 101/02* (2013.01); *A61F 2/04* (2013.01); *A61F 2250/0081* (2013.01); *A61L 2430/06* (2013.01); *A61L 2430/34* (2013.01); *B29C 64/112* (2017.08); *B29K 2001/00* (2013.01); *B29K 2089/00* (2013.01); *B29K 2995/0056* (2013.01); *B29L 2031/7532* (2013.01); *B82Y 5/00* (2013.01); *B82Y 15/00* (2013.01)

(58) Field of Classification Search
USPC ................... 424/464–499; 536/56; 426/658
See application file for complete search history.

(56) References Cited

U.S. PATENT DOCUMENTS

| | | | |
|---|---|---|---|
| 9,725,613 | B2 | 8/2017 | Garcia et al. |
| 2009/0022791 | A1* | 1/2009 | Obae .................... A61K 9/2018 424/464 |
| 2013/0309295 | A1 | 11/2013 | Gatenholm |
| 2015/0375453 | A1 | 12/2015 | Yost et al. |
| 2017/0079262 | A1 | 3/2017 | Rowley et al. |
| 2017/0216498 | A1 | 8/2017 | Kang et al. |
| 2017/0348458 | A1 | 12/2017 | Kesti et al. |
| 2017/0368225 | A1 | 12/2017 | Gatenholm |
| 2018/0273904 | A1 | 9/2018 | Skardal |
| 2019/0160203 | A1 | 5/2019 | Gatenholm |
| 2019/0209738 | A1 | 7/2019 | Gatenholm |

FOREIGN PATENT DOCUMENTS

| | | | |
|---|---|---|---|
| EP | 2975115 | A1 | 1/2016 |
| FI | 123988 | B | 1/2014 |
| HR | PK20140564 | A2 | 12/2015 |
| HR | PK20140564 | B | 5/2017 |
| JP | 2013181167 | A | 9/2013 |
| WO | 2008122661 | A1 | 10/2008 |
| WO | 2012056109 | A2 | 5/2012 |
| WO | 2012056111 | A2 | 5/2012 |
| WO | 2012071578 | A2 | 5/2012 |
| WO | 2012056110 | A3 | 6/2012 |
| WO | 2014049204 | A1 | 4/2014 |
| WO | 2015066705 | A1 | 5/2015 |
| WO | 2015175457 | A1 | 11/2015 |
| WO | 2016091336 | A1 | 6/2016 |
| WO | 2016100856 | A1 | 6/2016 |
| WO | 2017115056 | A1 | 7/2017 |
| WO | 2017210663 | A1 | 12/2017 |
| WO | 2018119989 | A1 | 7/2018 |
| WO | 2018169965 | A1 | 9/2018 |

OTHER PUBLICATIONS

Co-pending European Patent Application No. 15871191.1 filed Jul. 18, 2017.
Co-pending International Patent Application No. PCT/US15/66755 filed Dec. 18, 2015, published as WO 2016/100856 on Jun. 23, 2016.
Co-pending International Patent Application No. PCT/US15/66755, International Preliminary Report on Patentability dated Jun. 20, 2017, 6 pages.
Co-pending International Patent Application No. PCT/US15/66755, International Search Report and Written Opinion dated Apr. 28, 2016, 8 pages.
Gatenholm P. et al. Bacteria fabricate 3D scaffolds for organ regeneration, Symposium 13: Biomedical research. New Biotechnology, Jule 2014, vol. 31S, p. S52.
Murphy S. V et al. 3D bioprinting of tissues and organs. Nature Biotechnology, Aug. 2014, vol. 32, No. 8, p. 773-785.
Ventola C.L. Medical Applications for 3D Printing: Current and Projected Uses. P&T, Oct. 2014, vol. 39 No. 10, p. 704-711.
Helenius G, H. Backdahl, A. Bodin, U. Nanmark, P. Gatenholm, B. Risberg, In vivo Biocompatibility of Bacterial Cellulose, J. Biomed. Mater. Res. A., 76, 431-438, 2005.
Martinez, Hector Avila, S. Schwarz, E.M. Feldmann, A. Mantas, A. Von Bomhard, P. Gatenholm, and N. Rotter, Biocompatibility evaluation of densified bacterial nanocellulose hydrogel as an implant material for auricular cartilage regeneration. Appl. Microbiol. Biotechnol., 2014. 98(17): p. 7423-7435.
Petersen N, Gatenholm, P., Bacterial cellulose-based materials and medical devices: current state and perspectives, Applied Microbiology and Biotechnology, 91, 1277, 2011.
Co-pending European Patent Application No. 15871191.1, Supplemental Search and Opinion, dated Sep. 18, 2018, 8 pages.
D. Gethin, A. Rees et al., "Studies on the 3D Printing of Nanocellulose Structures", Advances in Printing and Media Technology, vol. XLI(I), A2, (2014), 91-95.
L.Nimeskern, et al., "Mechanical evaluation of bacterial nanocellulose as an implant material for ear cartilage replacement", Journal of the Mechanical Behaviour of Biomedical Materials, 22 (2013), 12-21.
Letter and Communication pursuant to Rule 114(2) EPC in Co-pending European Patent Application No. 15871191.1 filed Jul. 18, 2017, dated Jun. 12, 2018, 7 pages.
Co-pending European Patent Application No. 15871191.1, File History, Nov. 2019 to Feb. 2020, 30 pages.
Co-pending European Patent Application No. 15871191.1, File History, Oct. 2018 to Jul. 2019, 28 pages.
Co-pending International Patent Application No. PCT/US2017/035861 filed Jun. 3, 2017, International Preliminary Report on Patentability dated Dec. 4, 2018, 11 pages.
Co-Pending International Patent Application No. PCT/US2017/035861 filed Jun. 3, 2017, International Search Report and Written Opinion dated Aug. 17, 2017.
Huh et al "From 3D Cell Culture to Organs-on-Chips," Trends Cell Biol. Dec. 1, 2011 (Dec. 1, 2011), vol. 21,155.12, pp. 745-754.
J.A. Rowley, G. Madlambayan, D.J Mooney, Alginate hydrogels as synthetic extracellular matrix materials, Biomaterials 20 (1999), 45-53.
Jia et al. "Engineering Alginate as a Bioink for Bioprinting," Acta Biomater. Oct. 1, 2015 (Oct. 1, 2015), vol. 10, Iss. 10, pp. 4323-4331.

(56) References Cited

OTHER PUBLICATIONS

Kuzmenko, Y, S. Saemfors, D. Haegg, and P. Gatenholm, Universal method for protein bioconjugation with nanocellulose scaffolds for increased cell adhesion. Mater. Sci. Eng., C,2013. 33(8): p. 4599-4607.

Markstedt et al. "3D Bioprinting Human Chondrocytes with Nanocellulose-Alginate Bioink—for Cartilage Tissue Engineering Applications," Bio Macromolecules, Mar. 25, 2015 (Mar. 25, 2015) vol. 16, Iss. 5, pp. 1489-1496.

Nakamura et al. "Biomatrices and Biomaterials for Future Developments of Bioprinting and Biofabrication," Biofabrication, Mar. 10, 2010 (Mar. 10, 2010) vol. 2, Iss. 1, pp. 1-6.

Rutz et al. "A Multi-Material Bioink Method for 3D Printing Tunable, Cell-Compatible—Hydrogels," Adv Mater. Mar. 4, 2015 (Mar. 4, 2015), vol. 27, Iss. 9, pp. 1-18.

Salas, C et al. Nanocellulose properties and applications in colloids and interfaces. Current Opinion in Colloid and Interface Science Oct. 30, 2014, vol. 19, No. 5, pp. 383-396.

X Ahadjan et al. "Bioconjugated Hydrogels for Tissue Engineering and Regenerative Medicine," Bioconjuoate Chem. Jul. 15, 2015 (Jul. 15, 2015) vol. 26, Iss. 10, pp. 1984-2001.

X Panwar et al. "Current Status of Bioinks for Micro-Extrusion-Based 3D Bioprinting Molecules," Molecules, May 25, 2016 (May 25, 2016) vol. 21, Iss. 6, pp. 1-26.

Y Andrade et al. "Improving the Affinity of Fibroblasts for Bacterial Cellulose Using—Carbohydrate-Binding Modules Fused to RGD," Journal of Biomedical Materials Research. Jan. 22, 2009 (Jan. 22, 2009) vol. 92, Iss. 1, pp. 9-17.

(Gatenholm, Paul) Co-pending U.S. Appl. No. 16/777,146, filed Jan. 30, 2020, Specification, Claims, Figures.

(Gatenholm, Paul) Co-pending U.S. Appl. No. 16/799,062, filed Feb. 24, 2020, Specification, Claims, Figures.

Co-pending U.S. Appl. No. 16/777,146, Preliminary Amendment, filed Jan. 30, 2020, 5 pgs.

(Gatenholm, Paul) U.S. Appl. No. 16/306,436, filed Nov. 30, 2018, Specification, Claims, Figures.

(Gatenholm, Paul) U.S. Appl. No. 16/307,852, filed Dec. 6, 2018, Specification, Claims, Figures.

(Gatenholm, Paul) International Patent Application No. PCT/US17/035861 filed Jun. 3, 2017, published as WO 2017/210663 dated Dec. 7, 2017, Specification, Claims, Figures.

(Gatenholm, Paul) International Patent Application No. PCT/US17/036895, filed Jun. 9, 2017, which published as WO 2017/214592 dated Dec. 14, 2017, Specification, Claims, Figures.

(Martinez, Hector et al.) International Application No. PCT/US19/55684, filed Oct. 10, 2019, Specification, Claims, Figures.

(Redwan, Adel Itadele Namro et al.) International Application No. PCT/US19/58025, filed Oct. 25, 2019, Specification, Claims, Figures.

Avila, Hector Martinez et al. 3D bioprinting of human chondrocyte-laden nanocellulose hydrogels for patient-specific auricular cartilage regeneration. Bioprinting vol. 1-2, Mar. 1, 2016, pp. 22-35.

Bovine Collagen Solution, Sigma Aldrich, 2020, https://www.sigmaaldrich.com/catalog/product/aldrich/804614?lang=en&region=US. (International Search Report of PCT/US2019/055684 dated Jan. 28, 2020 indicates this reference was retrieved as early as Jan. 6, 2020. Retrieved Apr. 14, 2020.).

U.S. Appl. No. 16/777,146, Preliminary Amendment, filed Jan. 30, 2020, 5 pages.

International Application No. PCT/US19/55684, International Search Report and Written Opinion dated Jan. 28, 2020, 8 pages.

International Application No. PCT/US19/58025, International Search Report and Written Opinion dated Feb. 6, 2020, 10 pages.

International Patent Application No. PCT/US17/035861 International Search Report and Written Opinion dated Aug. 17, 2017, 14 pages.

International Patent Application No. PCT/US17/036895, International Search Report and Written Opinion dated Sep. 6, 2017, 9 pages.

Fink, Helen et al. Bacterial cellulose modified with xyloglucan bearing the adhesion peptide RGD promotes endothelial cell adhesion and metabolism-a promising modification for vascular grafts, Journal of Tissue Engineering and Regenerative Medicine, vol. 5, No. 6, Jun. 1, 2011, pp. 454-463.

Guerreiro, Susana G. et al. Neonatal Human Dermal Fibroblasts Immobilized in RGD-Alginate Induce Angiogenesis. Cell Transplantation, 23, 2014, 945-957.

Johnson, H. Y. Chung et al. Bio-ink properties and printability for extrusion printing living cells. Biomater. Sci. 2013, 1, 763-773.

Lee, K. Y. and Mooney, D. J. Alginate: Properties and biomedical applications. Progress in Polymer Science, 37, 2012,106-126.

Michael, S. et al. Tissue Engineered Skin Substitutes Created by Laser-Assisted Bioprinting Form Skin-Like Structures in the Dorsal Skin Fold Chamber in Mice. PLOS. Mar. 4, 2013; vol. 8, No. 3, pp. 1-12; doi:10.1371/jounal.pone.0057741.

Qing, Gao et al. Coxial nozzle-assisted 3D bioprinting with built-in microchannels for nutrients delivery. Biomaterials, 61, 2015, 203-215.

Xu, Mingen et al. An cell-assembly derived physiological 3D model of the metabolic syndrome, based on adipose-derived stromal cells and a gelatin/alginate/fibrinogen matrix. Biomaterials 31 (2010) 3868-3877.

Zhou, Y; The Application of Ultrasound in 3D Bio-Printing. Molecules. May 5, 2016, vol. 21 No. 590; pp. 1-25.

\* cited by examiner

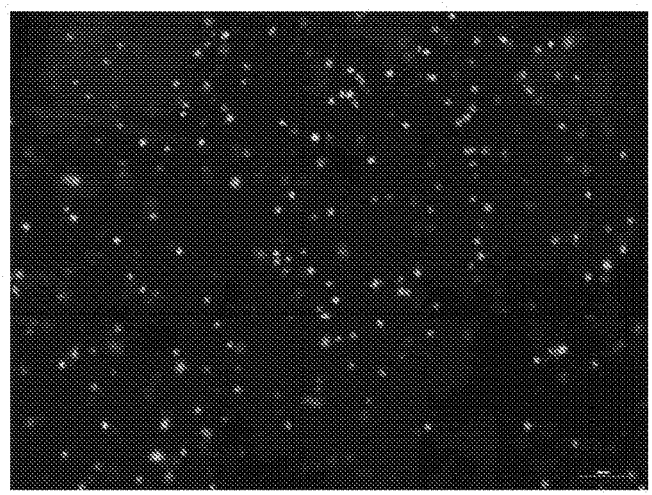
FIG. 7
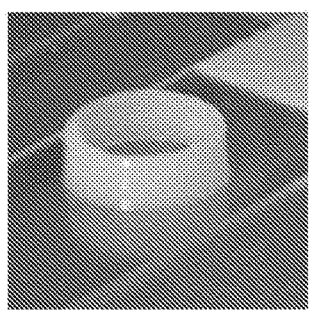 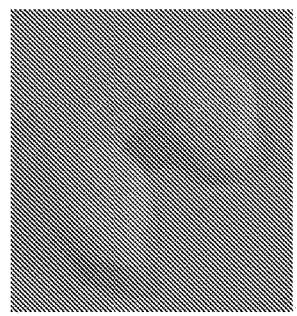 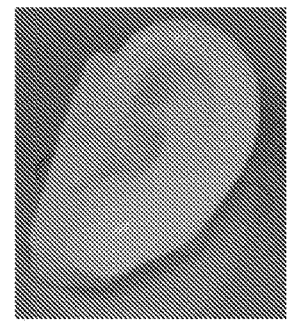
FIG. 8A        FIG. 8B        FIG. 8C

CELLULOSE NANOFIBRILLAR BIOINK FOR 3D BIOPRINTING FOR CELL CULTURING, TISSUE ENGINEERING AND REGENERATIVE MEDICINE APPLICATIONS

CROSS-REFERENCE TO RELATED APPLICATIONS

The present application is a National Stage application under 35 USC § 371 of International Application No. PCT/US15/66755 filed Dec. 18, 2015, which application relies on the disclosure of and claims priority to and the benefit of the filing date of U.S. Provisional Application No. 62/093,881, filed Dec. 18, 2014, the disclosures of each of which are hereby incorporated by reference herein in their entireties.

BACKGROUND OF THE INVENTION

Field of the Invention

The present invention relates to novel bioink which is biomaterial in the form of water dispersion of cellulose nanofibrils and can be converted into desired 3D shapes using 3D Bioprinting technology.

This novel bioink is suitable for 3D cell culturing and growing living tissues and organs. In this invention, cellulose nanofibrillar material is processed through different mechanical, enzymatic and/or chemical steps to yield fibril dispersion with desired rheological and morphological properties to be used as bioink in a 3D Bioprinter. The homogenization processes can be followed by purification of the material to yield biomaterial which has a desired level of cytocompatibility and can thus be combined with living cells.

Cellulose nanofibrils can be produced by a microbial process but can also be isolated from plant's secondary or primary cell wall, animals such as tunicates, algae and fungi. The desired parameters described in this invention are the size of fibril, the surface properties, concentration and biocompatibility. In this invention cellulose nanofibrils are combined with different additives which facilitate a crosslinking process to enhance mechanical properties of 3D Bioprinted structures. The nanocellulose bioink, CELLINK™, is typically prepared using sterile components and prepared in clean room conditions. The osmolarity of the CELLINK™ is designed to provide compatibility with mammalian cells. CELLINK™ can be 3D Bioprinted with cells or without cells. CELLINK™ can also be used to support other bioinks such as materials prepared from decellularized tissue and organs.

More particularly, embodiments of the invention relate to soft and hard tissue repair, scaffolds, systems and methods for the design, production, and control of the architecture and biomechanical properties of biomaterials which are used to grow tissue and organs. Specific embodiments of the invention relate to biocompatible materials, tissue engineering and regenerative medicine, implants, biomedical devices and health care products and, more particularly, to use as bioink in 3D Bioprinting processes to create optimal architecture and biomechanical performance of artificial tissues and organs. The present invention also relates to novel devices, systems and methods employing engineered tissues and/or organs having a desired 3D architecture and morphology supported by a 3D nanocellulose based scaffold, which can be used for high throughput drug discovery, screening, and toxicity testing. It can also be used to grow artificial tumor and thus used for in vitro cancer research.

Description of Related Art

Tissue engineering is using cells, supporting material—scaffolds, growth factors and in many cases bioreactors, to grow in vitro or in vivo tissue and organs. The driving force has been a shortage of organs which are needed for transplantation. Tremendous scientific and technological progress has been made in the past 20 years which has made it possible to grow almost all human tissues and many organs. In recent years the pharmaceutical and cosmetic industry has shown great interest in applying advances in tissue engineering to grow tissue and "mini" organs for drug discovery and drug testing. The new regulations are making restrictions for using animals for testing of cosmetic products. This has initiated tremendous interest for developing human skin models "skin on the plate".

The human cells should have a 3D environment similar to a native tissue environment to be able to migrate, proliferate, and/or differentiate to develop functional tissues. Likewise, stem cells typically need a 3D environment to differentiate into desired cell lineage. This is the reason why scaffolds with 3D architecture and specific microporosity have been developed for tissue engineering applications. In classical tissue engineering experiments, cells are seeded in a 3D scaffold and then cultivated in an incubator or stimulated in a bioreactor or directly implanted in vivo.

Many different synthetic and natural polymers have been evaluated as scaffolds for tissue engineering. Examples of biodegradable synthetic polymers include polylactic and polyglycolic acid. These polymers have often fast degradation characteristics and/or produce an environment which causes inflammation. Natural polymers include collagen, hyaluronic acid and its derivatives, alginate, and chitosan. While these materials can be fabricated into films, meshes, or more complex 3D structures, their successful use is limited by their physical and biochemical properties. Fabrication of 3D structures with controlled architecture and interconnected porosity has been challenging. The methods used, such as freeze drying, porogen removal or electrospinning, show poor reproducibility and lack of control of 3D architecture in micro scale. As the consequence of that, there have been difficulties in cell seeding since cell migration requires good pore interconnectivity.

In 3D printing processes, an object is fabricated layer by layer by a printer device using computer aided design, CAD file. 3D printing has been already successfully used in tissue engineering by many scientists to fabricate patient specific scaffolds. The scaffolds made of thermoplastic polymers have been extruded using 3D printers. The disadvantage of 3D printing using thermoplastic materials is a difficulty in cell seeding due to limited cell migration into porous structures. 3D Bioprinting operates using liquids in room or body temperature and thus can potentially handle living cells. The introduction of 3D Bioprinting is expected to revolutionize the field of tissue engineering and regenerative medicine, which might enable the reconstruction of living tissue and organs preferably using the patient's own cells. The 3D bioprinter is a robotic arm able to move in the X,Y,Z directions with a resolution of 10 μm while dispensing fluids. The 3D bioprinter can position several cell types and thus reconstruct the architecture of complex organs.

In U.S. Pat. No. 8,691,974 B2, entitled "Three-dimensional Bioprinting of Biosynthetic Cellulose Scaffolds for Tissue Engineering," a novel fermentation technique for controlling 3D shape, thickness and architecture of the entangled cellulose nanofibril network was presented. That patent described the use of a fermentation process to grow a 3D structure of biosynthetic cellulose. This technique can unfortunately not be combined with mammalian cells due to the differences in cultivation conditions at 37 degrees, which is required for mammalian cells, since bacterial cells are killed. Biosynthetic cellulose, BC is an emerging biomaterial for biomedical devices and implants (Petersen N, Gatenholm, P., Bacterial cellulose-based materials and medical devices: current state and perspectives, Applied Microbiology and Biotechnology, 91, 1277, 2011). The BC nanofibrils have a similar size and morphology as collagen (diameter 10-30 nm and length up to micrometers), which is very attractive for cell attachment, cell migration, and the production of Extracellular Matrix components. In vitro and in vivo studies have shown that BC implants typically do not elicit any foreign-body reaction, fibrosis, and/or capsule formation, and/or connective tissue integrates well with BC biomaterial (Helenius G, H. Bäckdahl, A. Bodin, U. Nanmark, P. Gatenholm, B. Risberg, In vivo Biocompatibility of Bacterial Cellulose, J. Biomed. Mater. Res. A., 76, 431, 2006; Martinez Avila, H., S. Schwarz, E. M. Feldmann, A. Mantas, A. Von Bomhard, P. Gatenholm, and N. Rotter, Biocompatibility evaluation of densified bacterial nanocellulose hydrogel as an implant material for auricular cartilage regeneration. Appl. Microbiol. Biotechnol., 2014. 98(17): p. 7423-7435.).

It is expected that a biosynthetic cellulose network cannot as such be used as a scaffold for tissue engineering because the relatively tight network of cellulose nanofibrils which make cell migration difficult to impossible. The biofabrication processes in which the macroporosity of 3D nanocellulose biomaterial has been developed by introducing porogens during the fermentation process has been described Bäckdahl, H., Esguerra, M., Delbro, D., Risberg, B., and Gatenholm, P., Engineering microporosity in bacterial cellulose scaffolds, Journal of Tissue Engineering and Regenerative Medicine, 2 (6), 320-330 (2008). The porogens have to be removed during purification process. None of the methods enable reproducible and scalable control of the architecture of the scaffolds or a convenient method to combine with the cells.

The development of high resolution 3D Bioprinters enables positioning of several human cell types with high accuracy and reproducibility and thus reconstruction of complex tissue and organs. Rapid advances in stem cell isolation from patient tissue, such as adipose, make it possible to have access to a sufficient amount of autologous cells for tissue repair in one step surgery. The cells typically cannot be printed alone since they are expected not to stay in place. As a result, the cells are suspended in culture medium or buffer, which has a low viscosity. In addition, the cells are preferably protected from high shear stresses in the printing head device. Furthermore, after printing, the cells should be in a cytocompatible environment, which will allow nutrients and oxygen to be administered to cells and preferentially provide support for cell attachment. When tissue with a desired 3D architecture on different length scales is desired, there is a need of a bioink capable of providing viscoelastic characteristic to be transferred in 3D scaffolds with predetermined shape. The bioinks are preferred to be developed and commercialized to secure a supply of printable and cell friendly scaffolds for tissue engineering and regenerative medicine applications.

SUMMARY OF THE INVENTION

In this invention processes for preparation of a new bioink, CELLINK™, for printing soft tissue and organs and use of this bioink in 3D Bioprinting processes of tissue and organs are described. In embodiments, the structure of human and animal soft tissue is mimicked by producing biomaterials with a desired architecture using semicrystalline cellulose nanofibrils. Cellulose nanofibrils can be isolated from wood material, annual plants, animals such as tunicates or can be produced by fungi or bacteria. This invention describes a new generation of water borne biomimetic printable biomaterial-scaffolds with unique printability into 3D shapes and ability to support tissue and organ growth.

Bioink, CELLINK™, as described in this invention is composed of a nanofibrillated cellulose dispersion with preferable addition of a crosslinking component. Such bioink can be crosslinked preferably after printing or even during the 3D bioprinting operation. In some applications CELLINK™ can be used without a crosslinking agent. CELLINK™ as described in this invention has unique rheological properties with extremely high zero shear rate viscosity and shear thinning behavior with fast recovery after shearing (printing operation). The viscosity of CELLINK™ can be tailor made by selecting a suitable concentration of cellulose nanofibrils, their length (aspect ratio), charge and additives. Desired cytotoxicity characteristics and cell viability characteristics have been developed by a purification process and adaptation of osmolarity of the dispersion in order to print CELLINK™ with living cells.

Several different types of mammalian cells including bovine fibroblasts, human chondrocytes and induced pluripotent stem cells have been successfully printed with CELLINK™ in complex 3D shapes of human organs, and the cells show good viability after printing and crosslinking. Long term evaluation (more than 28 days) showed human cartilage regeneration in 3D Bioprinted tissue. CELLINK™ has been also shown to be a great support material when printing complex tissues with collagen or decellularized matrix based bioinks. The biomimetic and biocompatibility characteristics of these novel nanocellulose fibrils based bioinks make them ideal candidates for applications in cell culture, tissue engineering and regenerative medicine.

BRIEF DESCRIPTION OF THE DRAWINGS

The accompanying drawings illustrate certain aspects of some of the embodiments of the present invention, and should not be used to limit or define the invention. Together with the written description the drawings serve to explain certain principles of the invention.

FIG. 7 is an image which shows excellent cell viability when human chondrocytes are mixed with CELLINK™ and 3D Bioprinted. The life-death assay was performed 6 days after printing.

FIG. 8A-C are images which show 3D cartilage organs printed with CELLINK™ A) trachea, B) meniscus, and C) ear.

DETAILED DESCRIPTION OF VARIOUS EMBODIMENTS OF THE INVENTION

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Embodiments of the present invention relate to biomaterial in liquid form (e.g., dispersions) defined as a bioink which can be used for 3D Bioprinting of scaffolds, tissues and organs. More particularly, embodiments of the invention include a method of making bioink from nanocellulose material and use of the bioink with and without cells to bioprint 3D scaffolds, 3D cell culture models, tissues and organs.

Embodiments of the invention include cellulose nanofibril bioink products prepared by the methods described and include using the products in 3D Bioprinting operations. Cellulose can be generated from plants (such as annual plants), trees, fungi or bacteria, with preferred embodiments generated from bacteria such as from one or more of the genera *Aerobacter, Acetobacter, Acromobacter, Agrobacterium, Alacaligenes, Azotobacter, Pseudomonas, Rhizobium,* and/or *Sarcina*, specifically *Gluconacetobacter xylinus, Acetobacter xylinum, Lactobacillus mali, Agrobacterium tumefaciens, Rhizobium leguminosarum* bv. *trifolii, Sarcina ventriculi, enterobacteriaceae Salmonella* spp., *Escherichia coli, Klebsiella pneu-moniae* and several species of cyanobacteria.

Figure 1:
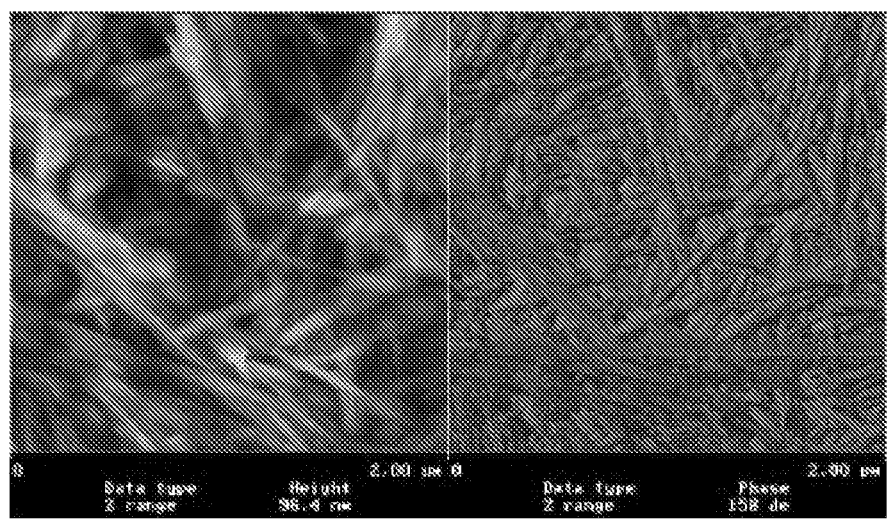
FIG. 1 is an AFM image of a Bacterial Cellulose nanofibrillar dispersion as prepared by hydrolysis. Microfibril size is: width 30 nm and length above 2 micrometers.
Figure 2:
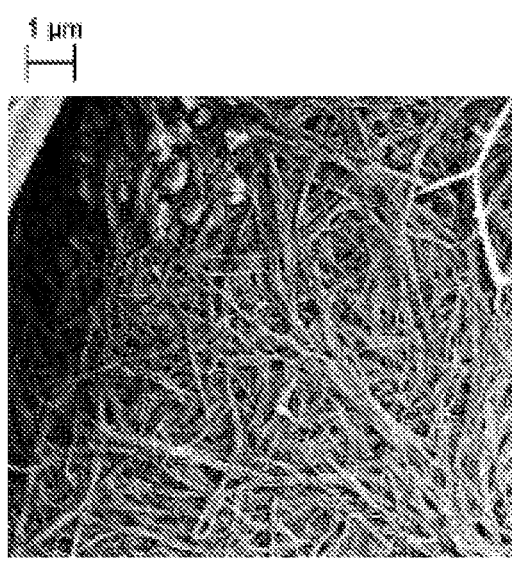
FIG. 2 is a Scanning Electron Microscopy (SEM) image of a Bacterial Cellulose nanofibrillar dispersion as prepared by hydrolysis. Microfibril is: width 30 nm and length above 10 micrometers.
Figure 3:
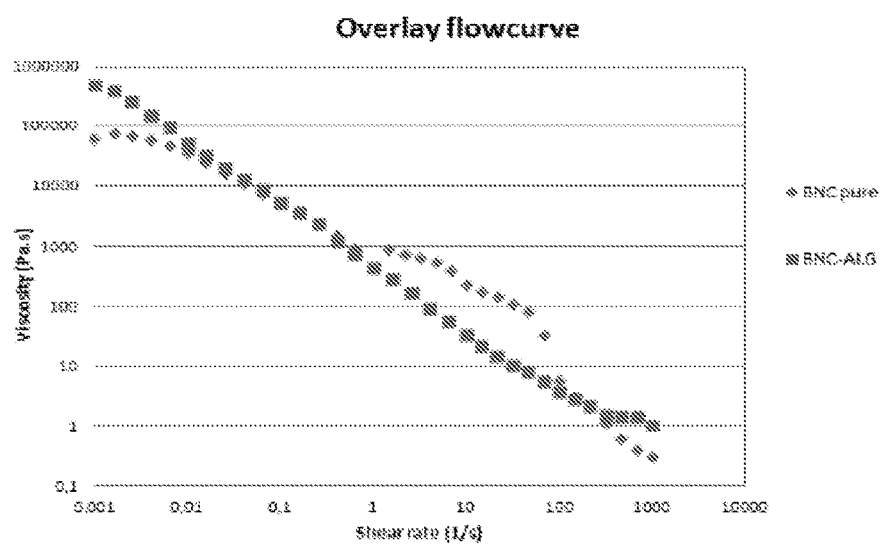
FIG. 3 is a graph which shows rheological properties of a BC nanofibrillar dispersion and BC/alginate bioink with extremely high zero shear viscosity and viscosity of 5 Pa·s (Pascal seconds) at 100 $s^{-1}$.
Figure 4A:
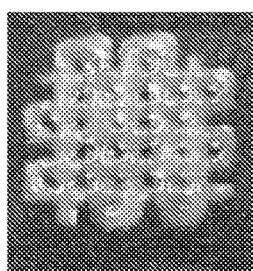
FIGS. 4A-C are images which show 3D Bioprinted scaffolds with BC nanofibrillar bioink a) without alginate, b) with alginate, c) with alginate, crosslinked. It shows good printability which is further improved by addition of alginate and crosslinking after printing.
Figure 4B:
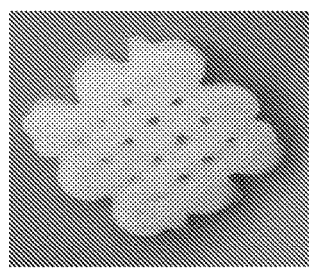
Figure 4C:
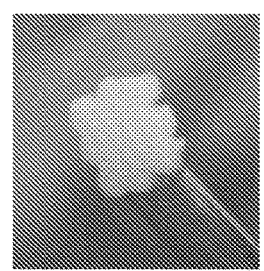

Cellulose can be generated from any vascular plant species, which include those within the groups *Tracheophyta* and *Tracheobionta*. Cellulose nanofibrils formed from cellulose producing bacteria most closely mimic the characteristics of collagen found in human and animal soft tissue. The array of fibrils provides a porous yet durable and flexible material. The nanofibrils allow nutrients, oxygen, proteins, growth factors and proteoglycans to pass through the space between the fibrils, allowing the scaffold to integrate with the implant and surrounding tissue. The nanofibrils also provide the elasticity and strength needed to replace natural collagen. The bacterial cellulose materials have been, after purification, homogenized and hydrolyzed to smooth dispersion. The continuous 3D network of typical bacterial cellulose pellicle has been disintegrated and the length of the fibrils has been reduced to 10-100 microns while the width of 30 nanometers has not been affected (see FIGS. 1 and 2). This mechanical homogenization combined with chemical hydrolyses contributed to formation of stable and very smooth dispersion with no clogging of the printer nozzle. The cellulose nanofibrils have been slightly surface modified with addition of sulphated groups which is advantageous to bind the growth factors and thus stimulate cell differentiation. The reduced fibril length made it possible to increase solid content up to 5-8% by weight. The dispersion had extremely high viscosity at zero shear and viscosity of about 10 Pa·s at $100^{s-1}$. That is what contributed to good printability. The nanocellulose dispersion can be 3D Bioprinted without addition of crosslinker as it can be seen in FIG. 4A. Addition of crosslinker such as alginate (20% based on NC) can be used to improve printability but also provide mechanical stability after crosslinking with 100 mM Calcium Chloride solution (see FIGS. 4B and 4C). The BC bioink has been purified by an ultrafiltration process and then diafiltrated using pyrogen free water. The osmolarity was adjusted for cells by dissolving of D-mannitol and making 4.6% of D-mannitol (w/v) aqueous solution.

Wood derived cellulose nanofibrils were selected as an alternative raw material for the preparation of cellulose nanofibrillated bioink. The difference is that they do not form three dimensional network and their width is lower (10-20 nanometers) and length is lower (1-20 micrometers). The disadvantage of the wood derived cellulose nanofibrils can be the presence of other wood biopolymers such as hemicelluloses which can affect cells and cause foreign body reaction. These dispersions should preferably therefore be purified by an extraction process and removal of the water phase. It is a sensitive process since it can lead to agglomeration of fibrils which can result in bioink which tends to clog the 3D bioprinter printing nozzle. In this invention homogenization is used followed by centrifugation and ultrafiltration to prepare bioink based on wood cellulose nanofibrils. It has been found that the optimal properties were achieved when dispersion with solid content above 2% dry matter were used.

Figure 5:
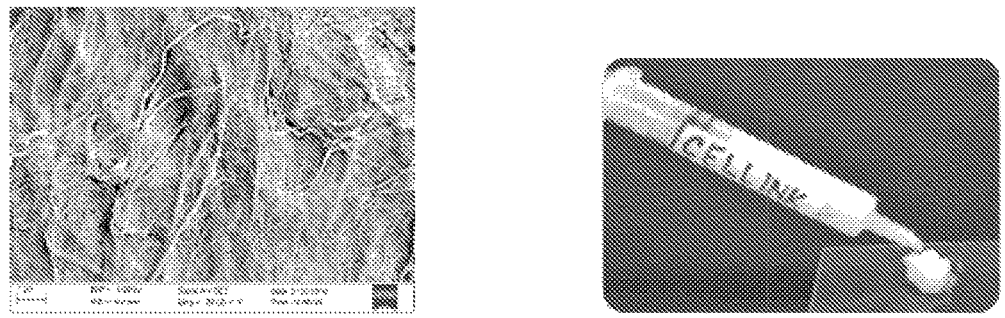
FIG. 5 is an image from a Scanning Electron Micrograph of Wood derived cellulose nanofbrillar (NFC) bioink and CELLINK™ in a cartridge ready for 3D Bioprinting. The Microfibril size is: width about 10 nm and length more than 10 micrometers. CELLINK™ in cartridge ready to use for bioprinting.

FIG. 5 is an image from a Scanning Electron Micrograph of Wood derived cellulose nanofbrillar (NFC) bioink and CELLINK™ in cartridge ready for 3D Bioprinting. The size of microfibrils is: width about 10 nm and length more than 10 micrometers. The CELLINK™ was prepared by addition of 20% alginate based on NFC dispersion and the osmolarity was adjusted by making 4.6% of D-mannitol (w/v) aqueous solution.

Figure 6A:
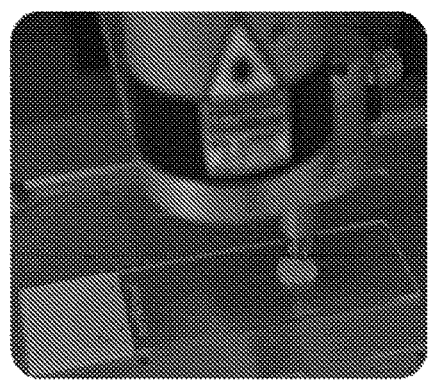
FIGS. 6A-B are images which respectively show 3D Bioprinting with regenHU Discovery 3D Bioprinter and NFC/alginate bioink, and printing fidelity of pure alginate and NFC/alginate bioink.
Figure 6B:
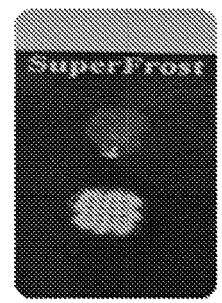
Figure 6C:
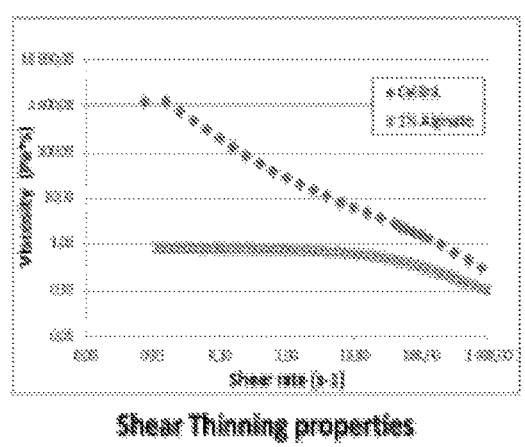
FIG. 6C is a graph which shows rheological properties of alginate and CELLINK™ based on NFC and alginate (80:20).

FIGS. 6A-C show 3D Bioprinting with regenHU Discovery 3D Bioprinter and NFC/alginate bioink, printing fidelity of pure alginate and NFC/alginate bioink and rheological properties of alginate and CELLINK™ based on NFC and alginate (80:20).

FIG. 7 shows excellent cell viability when human chondrocytes are mixed with CELLINK™ and 3D Bioprinted. The life-death assay was performed 6 days after printing.

FIGS. 8A-C show 3D cartilage organs such as trachea, meniscus and ear printed with CELLINK™.

Figure 9:
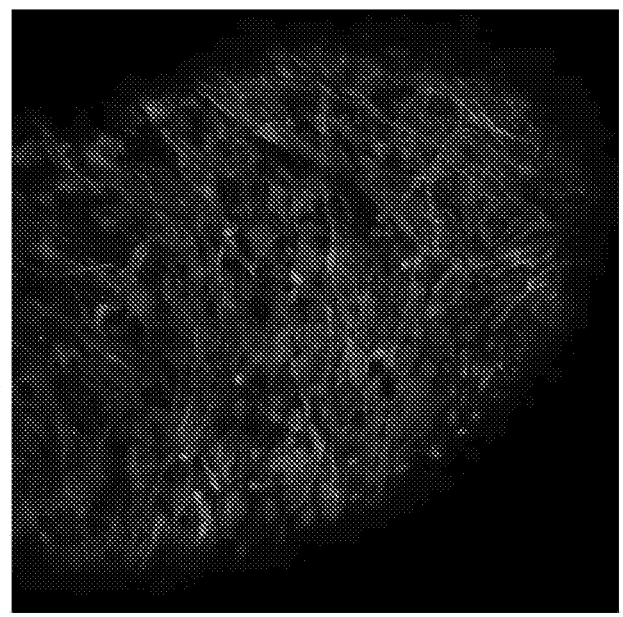
FIG. 9 is a confocal microscopy image of Human Chondrocytes in 3D bioprinted NFC/alginate bioink after 30 days culture.

FIG. 9 shows a confocal microscopy image of Human Chondrocytes in 3D bioprinted NFC/alginate bioink after 30 days culture. The cells have proliferated and are very healthy as it can be seen from their shape.

Figure 10:
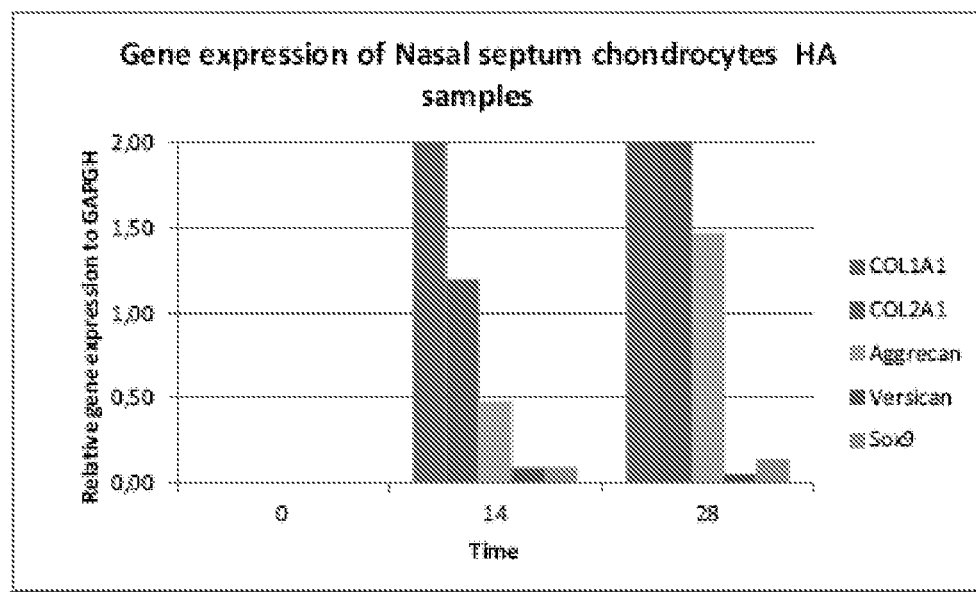
FIG. 10 is a graph which shows evidence of neocartilage production by Human Chondrocytes in 3D Bioprinted CELLINK™ after 30 days incubation. The presence of Collagen II provides evidence of cartilage production.

FIG. 10 shows evidence of neocartilage production by Human Chondrocytes in 3D Bioprinted CELLINK™ after 30 days incubation. The presence of Collagen II is an evidence of cartilage production.

Figure 11:
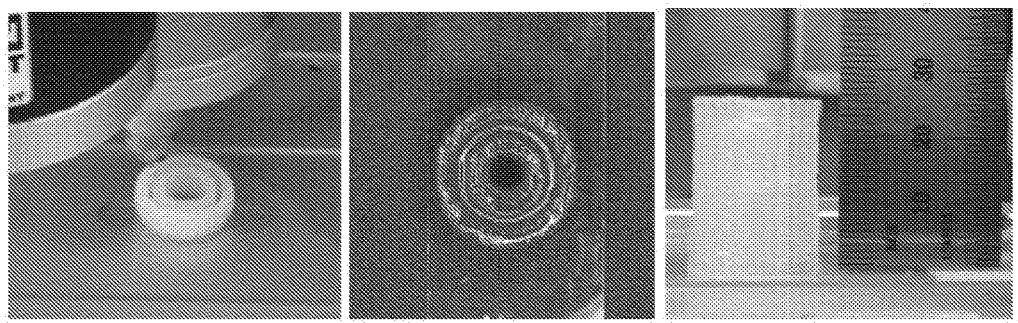
FIG. 11 provides images which show how cellulose nanofibrillated ink is used to 3D Bioprint and support tubular organs fabricated with collagen.

Another advantage of cellulose nanofibrillated bioink is when it is used as support material for printing of collagen bioink or by printing of extracellular matrix as it is shown in FIG. 11. The cellulose bioink keeps its 3D shape due to its extreme shear thinning properties. This allows for printing of a complex 3D support, which can, after formation of collagen or extracellular matrix, be easily removed.

Additionally, embodiments may allow formation and diffusion of proteoglycans within the structure to provide viscoelastic properties. Nutrients, oxygen, proteins, growth factors and proteoglycans can pass and diffuse through the space between the fibrils. Embodiments are designed to allow cells to stay in the bioink and are able to support extracellular matrix production which results in tissue formation without contraction.

Another advantageous characteristic of embodiments of the invention is that they can be non-degradable (e.g., tend not to degrade). Most biologically occurring materials are degradable, meaning they will break down or deteriorate over time, which can be problematic for use as disease models, for drug screening or for soft tissue repair. A non-degradable biological material provides a biologically compatible scaffold that will tend to maintain structure and function, or maintain structure and/or function for a desired period of time (such as the length of anticipated testing). Moreover, embodiments provide materials with good mechanical properties, which properties are desired for use of the constructs as implants.

To facilitate a better understanding of the present invention, the following examples of certain aspects of some embodiments are given. In no way should the following examples be read to limit, or define, the scope of the invention.

EXAMPLE 1

Preparation of Bacterial Cellulose (BC) Bioink and 3D Bioprinting

Tray bioreactors were inoculated with *Gluconacetobacter xylinus* ATCC® 700178. A suspension of $4 \times 10^6$ bacteria per ml and 25 ml of sterile culture media (described below) was added to each tray. The controlled volumes of sterilized media were added at each 6 hour increment to the top of the tray in such a manner that bacteria cultivation was preferably not disturbed. For example, the preferential addition is to use microspray, where media is added with a low pressure spray, mist, sprinkle or drip. The amount of the added media is calculated to be equivalent at least to an amount expected to be consumed by the bacteria during a 6 hour time period. The composition of the medium can be varied in order to control production rate of cellulose and network density. The trays were placed in a bacteriology cabinet and the bacteria were allowed to grow under these semi-dynamic conditions for 7 days at 30° C. The bacteria were removed by immersing the pellicles in 0.1 sodium carbonate overnight, followed by 24 h in fresh 0.1M NaOH heated in a 60° C. water bath. The samples were then carefully rinsed with large amounts of 60° C. deionized water to remove bacterial residues and neutralize the pH using acetic acid. After cleaning, the BC scaffolds were cut in rectangular scaffolds (1×1 cm).

Examples of suitable media for growing bacteria include but are not limited to: Schramm-Hestrin-medium which contains, per liter distilled water, 20 g of glucose, 5 g of bactopeptone, 5 g of yeast extract, 3.4 g of disodium-hydrogenphosphate dehydrate and 1.15 g of citric acid monohydrate and which exhibits a pH value between 6.0 and 6.3; 0.3 wt % green tea powder and 5 wt % sucrose with pH adjusted to 4.5 with acetic acid; Medium composed of (fructose [4% w/vol], yeast extract [0.5% w/v], (NH4)2SO4 [0.33% w/v], $KH_2PO_4$ [0.1% w/v], $MgSO_4.7H_2O$ [0.025% w/v], corn steep liquor [2% v/v], trace metal solution [1% v/v, (30 mg EDTA, 14.7 mg $CaCl_2.2H2O$, 3.6 mg $FeSO_4.7H_2O$, 2.42 mg $Na_2MoO_4.2H_2O$, 1.73 mg $ZnSO_4.7H_2O$, 1.39 mg $MnSO_4.5H_2O$ and 0.05 mg $CuSO_4.5H_2O$ in 1 liter distilled water)] and vitamin solution [1% v/v (2 mg inositol, 0.4 mg pyridoxine HCl, 0.4 mg niacin, 0.4 mg thiamine HCl, 0.2 mg para-aminobenzoic acid, 0.2 mg D-pantothenic acid calcium, 0.2 mg riboflavin, 0.0002 mg folic acid and 0.0002 mg D-biotin in 1 liter distilled water)]) provides good growth. Then the cut pellicles were disintegrated with a homogenizer. The suspension resulted in 371 g of BC pulp (1% cellulose content) in which 220 g of sulfuric acid (98% pure) was added to start the hydrolysis process. The mixture was placed in an oil bath (60° C.) on a stirrer for 48 hours. Then 1.1 liter of DI water was added and centrifuged at 3500 rpm for about 30 min. After centrifugation the water was decanted and 1.1 liter of DI water was added and centrifuged at 3500 rpm for about 30 min. This procedure was repeated 3 times. After last centrifugation, 1.1 liter of DI water was added to the mixture and was neutralized with 0.1M NaOH and centrifuged at 3500 for 30 min. Then the water was decanted and 1.1 liter of water was added to the mixture. An IKA Ultra-turrax homogenizer was used for homogenization. The homogenized mixture was filtered with the use of an ultrafiltration using 30000 DA cellulose membranes. The filtrated/concentrated BNC-ink was finally placed at 4° C. until use. The final product is estimated to be around 70 ml out of initial 371 gr of BNC pulp. The continuous 3D network of typical bacterial cellulose pellicle has been disintegrated and the length of the fibrils has been reduced to 10-100 microns while the width of 30 nanometers has remained about the same as before processing (see FIGS. 1 and 2). This mechanical homogenization combined with chemical hydrolyses contributed to formation of stable and very smooth dispersion with no clogging of the printer nozzle. Little to no clogging of the printer nozzle is highly desired. The cellulose nanofibrils have been slightly surface modified with addition of sulphated groups which is advantageous to bind the growth factors and thus stimulate cell differentiation. The reduced fibril length made it possible to increase solid content up to 5-8% by weight. The dispersion had extremely high viscosity at zero shear and viscosity of about 10 Pa·s at $100^{s-1}$. That is what is believed to have contributed to good printability. The BC bioink has been purified by an ultrafiltration process and then diafiltrated using pyrogen free water. The osmolarity for compatibility with mammalian cells was achieved by adding D-mannitol to make 4.6% of D-mannitol (w/v) solution. The sterility of BC bioink was achieved by autoclaving at 120° C. for 30 minutes. The nanocellulose dispersion can be 3D Bioprinted without addition of crosslinker as it can be seen in FIG. 4A. Addition of crosslinker such as alginate (20% based on NC) improve printability but also provide mechanical stability after cross-linking with 100 mM Calcium Chloride solution (see FIGS. 4B and 4C).

EXAMPLE 2

Preparation of Bioink Based on Wood Derived Nanocellulose and 3D Bioprinting with Human Chondrocytes Cellulose nanofibrils (NFC) dispersion produced by mechanical refinement and enzymatic treatment was used as raw material for bioink preparation. The charge density of the NFC was determined to be 24 µeq/g. The NFC dispersion was purified using ultrafiltration followed by diafiltration with pyrogen free water. The NFC dispersion was further homogenized using Ultra turrax homogenizer and the concentration was brought to 2.5% by centrifugation (JOUAN CR 3i multifunction, Thermo Scientific) and removal of excess supernatant. The centrifugation was carried out at 4000 rpm for 10-20 minutes until the desired amount of supernatant was reached. The concentrated NFC was mixed intensely by stirring with a spatula for 10 minutes and autoclaved (Varioklav Steam Sterilizer 135T, Thermo Scientific) at liquid setting, 120° C. for 30 minutes. Alternative sterilization procedure was evaluated using electron beam (EB) sterilization at 25 kGy. No effect on viscosity or stability of NFC dispersion was observed by these two methods of sterilization. The optimal size of the NFC fibrils to be used as a bioink was determined using SEM, see FIG. 5. The fibril width was between 10 and 20 nanometers and length about 1 micron. They were however some fibrils with length up to 10 micrometers. In embodiments and for certain applications, it is extremely important that the NFC dispersion has good stability and does not contain agglomerates which can otherwise cause clogging of the printer nozzle. NFC dispersion was adjusted with regards to osmolarity for compatibility with mammalian cells by adding D-mannitol to make 4.6% of D-mannitol (w/v) solution. NFC dispersion was then mixed with sterile alginate at various ratios. The optimal composition was found to be 80:20 ratio between NFC and alginate. Such prepared bioink was then transferred at aseptic conditions in LAF bench to sterile printing cartridge. FIG. 5 also shows such bioink called CELLINK™ ready to use for 3D Bioprinting experiments and the consistency of the bioink is also visualized in FIG. 5. The rheological properties of the bioinks and their main components were analyzed using the Discovery HR-2 rheometer (TA Instruments, UK) with a peltier plate. All measurements were performed at 25° C. and the samples were allowed to reach equilibrium temperature for 60 s prior each measurement. For determination of the viscosity a cone-plate (40 mm, 1.99°) was used. The shear viscosity was measured at shear rates from 0.01 $s^{-1}$ to 1000 $s^{-1}$. The rheological properties are displayed in FIG. 6C. It is seen that CELLINK™ has very high zero shear viscosity and is extremely shear thinning. Optimal viscosity for good shape fidelity is between 1 and 50 Pa·s at 100 s-1. This shear rate is expected in the nozzle of 3D Bioprinter used in this study. FIG. 6C compares the shear thinning properties of CELLINK™ with pure alginate component which has not such high zero shear viscosity. This is reflected in printing fidelity as seen in FIG. 6B. The bioink composed of pure alginate shows no print fidelity. The bioink was printed using the 3D bioprinter 3D Discovery from regenHU (Switzerland) as seen in FIG. 6A. The printer head consisted of a microvalve with a 300 µm nozzle which dispensed the bioink in x, y and z direction. The flow rate was controlled by monitoring the feed rate (10-20 mm/s) the pressure (20-60 kPa), the valve opening time (400-1200 µs), and the dosing distance (0.05-0.07 mm). The CELLINK™ has been mixed under aseptic conditions using LAF bench with human nasal septum chondrocytes. CELLINK™ with 5 M cells per ml was prepared and gridded scaffolds (6×5 mm, line spacing 1 mm, 5 layers) were printed (30 kPa, feedrate 5 mm/s, dosing distance 0.07 mm, valve opening time 1200 µs) with approximately 300 K cells per scaffold. After printing, the scaffolds were crosslinked in 90 mM $CaCl_2$ solution for ten minutes. The $CaCl_2$ solution was thereafter removed; the scaffolds were rinsed once in complete medium and thereafter kept in complete medium, replaced three times a week. At day 6, Live/Dead staining was performed as per manufactures instructions (Molecular probes/Life technologies, #R37601). Viability was analyzed by calculating the live and the dead cells in five images from each time point. FIG. 7 shows excellent cell viability (more than 70%). The grids as shown in FIG. 6B were designed in the BioCAD software provided by regenHU. More complex 3D structures, tube for tracheal replacement, sheep meniscus and human ear were printed by converting Stereolithography (STL)—files into G-code used by the 3D Discovery Bioprinter. FIGS. 8A-C show excellent shape retention when printed these complex 3D structures. Samples were not crosslinked during printing. They were first crosslinked after printing by placing objects in 90 mM $CaCl_2$ solution for ten minutes. Some of the printed grids with chondrocytes cells were incubated for 28 days. FIG. 9 shows even cell distribution and excellent cell viability after 28 days culturing in crosslinked CELLINK grids. The prints kept good integrity and good mechanical properties. The analysis with rPCR, see FIG. 10 shows production of Collagen II and proteoglycans which increased after 28 days which is an evidence of growth of neocartilage in 3D bioprinted grids with CELLINK.

EXAMPLE 3

Printing of Support Using Nanocellulose Bioink

In order to evaluate the ability of using nanocellulose bioink as support for complex structures which could be produced with other materials such as collagen or extracellular matrix the following experiment was performed. Cellulose nanofibrillated ink was formulated with higher solid content (above 2.5%) to provide extremely high viscosity. The inner tubular structure for aorta or trachea was printed using cellulose bioink and then the outer tubular structure was printed with cellulose bioink. After each 500 micrometers the collagen was printed with another printing head between the two circles. The collagen ink, Bioink from regenHU was used and crosslinked using UV. This process continued until a desired length of tube was achieved. The cellulose bioink was not crosslinked and thus could be easily removed after printing process. This procedure was then evaluated to print with extracellular matrix which came from decellularized aorta. The autologous extracellular matrix can be loaded with autologous cells and tissue and organs ready for implantation to patient can be printed this way. This is shown in FIG. 11.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A cellulose nanofibril bioink comprising:
   a dispersion of cellulose nanofibrils in a liquid media, wherein the cellulose nanofibrils have a length of about 1-100 microns and a width of about 10 nanometers to 20 microns;
   a viscosity of between 1 and 50 Pa·s at 100 s$^{-1}$ at room temperature; and
   a solids content of up to 5-8% by weight of the dispersion.

2. The cellulose nanofibril bioink of claim 1, wherein the cellulose nanofibrils have an average length of about 1-20 microns and an average width of about 10-20 nanometers.

3. The cellulose nanofibril bioink of claim 1 comprising one or more biopolymers chosen from collagen or elastin.

4. A method comprising:
   providing a cellulose nanofibril bioink comprising:
      a dispersion of cellulose nanofibrils n a liquid media, wherein the cellulose nanofibrils have a length of about 1-100 microns and a width of about 10 nanometers to 20 microns;
      a viscosity of between 1 and 50 Pa·s at 100 s$^{-1}$ at room temperature; and
      a solids content of up to 5-8% by weight of the dispersion; and
   bioprinting a 3D construct with the cellulose nanofibril bioink as a support.

5. The method of claim 4, wherein the 3D bioprinting comprises 3D bioprinting of scaffolds, tissues, and/or organs.

6. The method of claim 4, wherein the 3D bioprinting comprises 3D bioprinting with cells.

7. The method of claim 4, wherein the 3D bioprinting comprises 3D bioprinting without cells.

8. The method of claim 6, wherein the cells are human cells.

9. The method of claim 4, further comprising reinforcing a tissue or organ with the 3D construct.

10. The method of claim 9, wherein the tissue or organ is a human or animal tissue or organ.

11. The method of claim 4, wherein the 3D construct is an organ.

12. The method of claim 11, further comprising implanting the organ into a human or animal.

13. The bioink of claim 3, wherein the one or more biopolymers is collagen.

14. The bioink of claim 1, further comprising cells.

15. The bioink of claim 14, wherein the cells are adapted to be human cells.

16. The bioink of claim 14, wherein the cells are adapted to be living cells.

17. The bioink of claim 14, wherein the cells are chosen from bovine fibroblasts, human chondrocytes, and/or induced pluripotent stem cells.

18. The bioink of claim 1, wherein the cellulose nanofibrils are chosen from animal, algae, plant, tree, fungus, wood, and/or bacteria type cellulose nanofibrils.

19. The bioink of claim 18, wherein the cellulose nanofibrils are chosen from bacteria type cellulose nanofibrils.

20. The bioink of claim 19, wherein the bacteria is chosen from *Acetobacter, Acromobacter, Agrobacterium, Alacaligenes, Azotobacter, Pseudomonas, Rhizobium, Sarcina, Gluconacetobacter xylinus, Acetobacter xylinum, Lactobacillus mali, Agrobacterium tumefaciens, Rhizobium leguminosarum* bv. *trifolii, Sarcina ventriculi, enterobacteriaceae Salmonella* spp., *Escherichia coli, Klebsiella pneumoniae* and/or cyanobacteria.

21. The bioink of claim 18, wherein the cellulose nanofibrils are chosen from *Tracheophyta* and *Tracheobionta* type cellulose nanofibrils.

22. The composition bioink of claim 1, further comprising a crosslinking agent.

23. The bioink of claim 1, further comprising alginate.

24. The bioink of claim 1, further comprising alginate and a crosslinking agent.

25. The bioink of claim 23, wherein the ratio of cellulose nanofibrils to alginate is about 80:20.

26. The bioink of claim 1, wherein the viscosity is about 10 Pa·s at 100 s−1.

27. The bioink of claim 1, wherein solids content ranges from about 1-3% by weight of the dispersion.

28. The bioink of claim 1, wherein the cellulose nanofibrils comprise sulphated groups.

29. The bioink of claim 18, wherein the cellulose nanofibrils are animal type cellulose nanofibrils from tunicates.

30. The method of claim 4, wherein the cellulose nanofibrils are chosen from animal, algae, plant, tree, fungus, wood, and/or bacteria type cellulose nanofibrils.

31. The method of claim 30, wherein the cellulose nanofibrils are chosen from bacteria type cellulose nanofibrils.

32. The method of claim 30, wherein the cellulose nanofibrils are animal type cellulose nanofibrils from tunicates.

* * * * *